(12) United States Patent
Xu et al.

(10) Patent No.: US 9,955,971 B2
(45) Date of Patent: May 1, 2018

(54) METHOD FOR TREATING AORTIC ARCH DISEASES

(71) Applicant: Lifetech Scientific (Shenzhen) Co., Ltd., Shenzhen (CN)

(72) Inventors: Zhiyun Xu, Shenzhen (CN); Xiangman Zhang, Shenzhen (CN); Lin Han, Shenzhen (CN); Deyuan Zhang, Shenzhen (CN); Benhao Xiao, Shenzhen (CN)

(73) Assignee: Lifetech Scientific (Shenzhen) Co. Ltd. (CN)

( * ) Notice: Subject to any disclaimer, the term of this patent is extended or adjusted under 35 U.S.C. 154(b) by 101 days.

(21) Appl. No.: 14/984,084

(22) Filed: Dec. 30, 2015

(65) Prior Publication Data

US 2017/0189030 A1    Jul. 6, 2017

(51) Int. Cl.
*A61F 2/856* (2013.01)
*A61B 17/11* (2006.01)
*A61F 2/07* (2013.01)
*A61B 17/12* (2006.01)
*A61F 2/06* (2013.01)

(52) U.S. Cl.
CPC .............. *A61B 17/11* (2013.01); *A61F 2/07* (2013.01); *A61F 2/856* (2013.01); *A61B 2017/1107* (2013.01); *A61B 2017/1132* (2013.01); *A61B 2017/12004* (2013.01); *A61F 2002/061* (2013.01); *A61F 2002/075* (2013.01)

(58) Field of Classification Search
CPC ........................... A61F 2/856; A61F 2250/001
See application file for complete search history.

(56) References Cited

U.S. PATENT DOCUMENTS 6,723,116 B2 * 4/2004 Taheri .............. A61B 17/00234
623/1.11

FOREIGN PATENT DOCUMENTS

CN         103720529 A  *  4/2014  ............... A61F 2/90

OTHER PUBLICATIONS

Translation of Chinese patent CN103720529 to Wang et al published Apr. 2014.*

* cited by examiner

*Primary Examiner* — Paul Prebilic
(74) *Attorney, Agent, or Firm* — Raymond Sun (57) ABSTRACT

In a method for treating an aortic arch disease, after an intraoperative stent is expanded in an aorta and at least one arch branch vessel, and before the vessel is exactly anastomosed with an incision, by blocking a thoracic aorta between the incision and an arch branch vessel closest to the incision, the intraoperative stent in the thoracic aorta is also blocked, so that blood is prevented from flowing from the incision, and a proximal orifice of the intraoperative stent, and the low body perfusion may be recovered in advance, thereby reducing the circulatory arrest time of the low body perfusion and reducing the time of ischemia of visceral organs and lower limbs of a patient. Meanwhile, the flow of a cerebral perfusion through the right axillary artery may be recovered to a normal flow in advance, and the time of ischemia of the brain of the patient is reduced.

9 Claims, 6 Drawing Sheets

METHOD FOR TREATING AORTIC ARCH DISEASES

TECHNICAL FIELD

The present invention relates to a method for treating aortic arch diseases, and in particular to a method for treating aortic arch diseases by using stents in conjunction with surgical methods and endovascular techniques.

BACKGROUND OF THE PRESENT INVENTION

Aortic diseases, mainly including aortic dissection and aortic aneurysm, are very dangerous diseases, with a mortality higher than 50% after the diseases come on within 48 hours, and a mortality higher than 85% after the diseases come on within two weeks, so the diseases pose serious threats to the human health. With the arrival of the aging trend in China, the mortality rates will constantly rise.

Stanford A aortic dissection is one common disease among the aortic arch diseases and occupies about 70% of the whole dissection diseases. At the aortic arch, a human body generally has three arch branch vessels for supplying blood to the brain, and it is required to establish a blood extracorporeal circulation during a surgery to maintain the blood supply to the brain, so it is very difficult to perform an operation at the aortic arch. At present, in addition to thoracotomy, a hybrid method may also be utilized to implant a replacement stent at a lesion site of the aortic arch so as to treat the aortic arch diseases. The hybrid method combines a surgical method with an endovascular technique. Compared with the pure surgical method, there are few anastomotic stomas (generally only one), and the hybrid method not only may greatly shorten the time of a surgical operation and the time of a corresponding extracorporeal circulation and also significantly reduce the amount of bleeding, but also may avoid the damage to the recurrent laryngeal nerve during operation, so that it is advantageous for the postoperative recovery of patients and the improvement of safety and effectiveness of operations.

Although the hybrid method reduces both the time of operation and the difficulty of the operation in comparison to a pure thoracotomy, it is still required to recover the low body perfusion (e.g., femoral artery perfusion) after the vessel is completely anastomosed and to recover the flow of a cerebral perfusion through the right axillary artery to a normal flow. Therefore, the time of circulatory arrest and the time of the cerebral perfusion time which is less than the normal perfusion amount are still long, so the surgical risk is relatively high.

SUMMARY OF THE PRESENT INVENTION

In view of the deficiencies in the prior art, the technical problem to be solved by the present invention is to provide a therapy for treating an aortic arch disease with short circulatory arrest time.

To solve the above technical problem, the present invention employs the following technical solutions: a method for treating an aortic arch disease is provided, including the following steps of:

establishing an extracorporeal circulation, the extracorporeal circulation including a low body perfusion and a normal-flow cerebral perfusion;

forming an incision on an ascending aorta, and stopping the low body perfusion;

delivering a distal section of an intraoperative stent into an aortic arch and at least one arch branch vessel through the incision by an endovascular technique, and radially expanding the distal section of the intraoperative stent;

blocking a thoracic aorta between the incision and the arch branch vessel closest to the incision;

recovering the low body perfusion;

surgically anastomosing a proximal section of the intraoperative stent with the ascending aorta and closing the incision; and releasing the blocked thoracic aorta.

In the method for treating an aortic arch disease according to the embodiments of the present invention, the forming an incision on an ascending aorta includes: cutting the cross-section of the ascending aorta, or forming a through hole on a wall of the ascending aorta.

In the method for treating an aortic arch disease according to the embodiments of the present invention, the endovascular technique includes: radially compressing the intraoperative stent into a sheath canal and delivering the intraoperative stent into a vessel through the sheath canal.

In the method for treating an aortic arch disease according to the embodiments of the present invention, the flow of the cerebral perfusion is reduced while forming the incision.

In the method for treating an aortic arch disease according to the embodiments of the present invention, an opening of any arch branch vessel is substantially unexposed by the incision.

In the method for treating an aortic arch disease according to the embodiments of the present invention, the method further includes the following step of: exhausting air after blocking a thoracic aorta between the incision and the arch branch vessel closest to the incision.

In the method for treating an aortic arch disease according to the embodiments of the present invention, the method includes: tying by a band or gripping by a pair of forceps the thoracic aorta between the incision and an arch branch vessel closest to the incision to block the thoracic aorta and the intraoperative stent in the thoracic aorta.

In the method for treating an aortic arch disease according to the embodiments of the present invention, the method further includes the following step of: recovering the flow of the cerebral perfusion to a normal flow after blocking a thoracic aorta between the incision and the arch branch vessel closest to the incision.

In the method for treating an aortic arch disease according to the embodiments of the present invention, the surgical anastomosis includes at least one of suturing, binding, winding with a thread, gripping and splicing.

In the method provided by the present invention, after the intraoperative stent is released and expanded in an aorta and at least one arch branch vessel, and before the vessel is exactly anastomosed with the incision, by blocking a thoracic aorta between the incision and an arch branch vessel closest to the incision, the intraoperative stent in the thoracic aorta is also blocked, so that blood is prevented from flowing from the incision and a proximal orifice of the intraoperative stent, and the low body perfusion (for example, femoral artery perfusion) may be recovered in advance, thereby reducing the circulatory arrest time of the low body perfusion and reducing the time of ischemia of visceral organs and lower limbs of a patient.

BRIEF DESCRIPTION OF THE DRAWINGS

The present invention will be further described below with reference to the accompanying drawings and embodiments, in which.

DETAILED DESCRIPTION OF THE PRESENT INVENTION

To understand the technical features, objectives and effects of the present invention more clearly, specific implementations of the present invention will be described in detail with reference to the accompanying drawings. For convenience, in the following description, the distal direction and the proximal direction are defined by a common method in this art. That is, the blood flows from a proximal end to a distal end.

Figure 1:
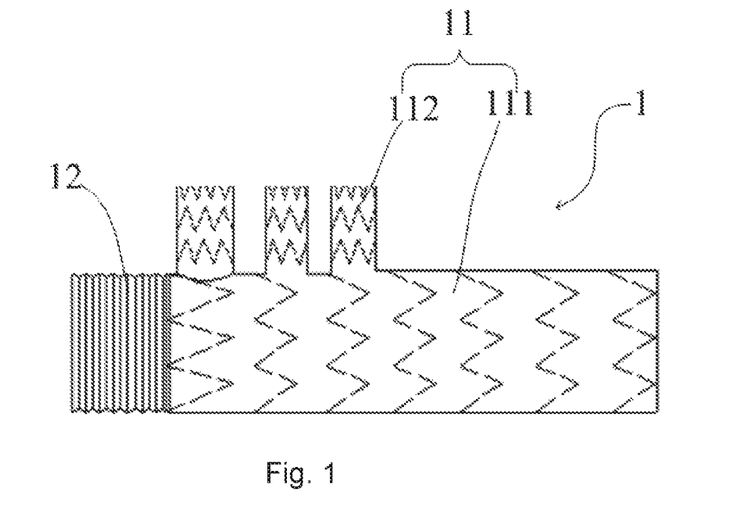
FIG. 1 is a structural diagram of an exemplary intraoperative stent that can be used in a method according to an embodiment of the present invention.
Figure 2:
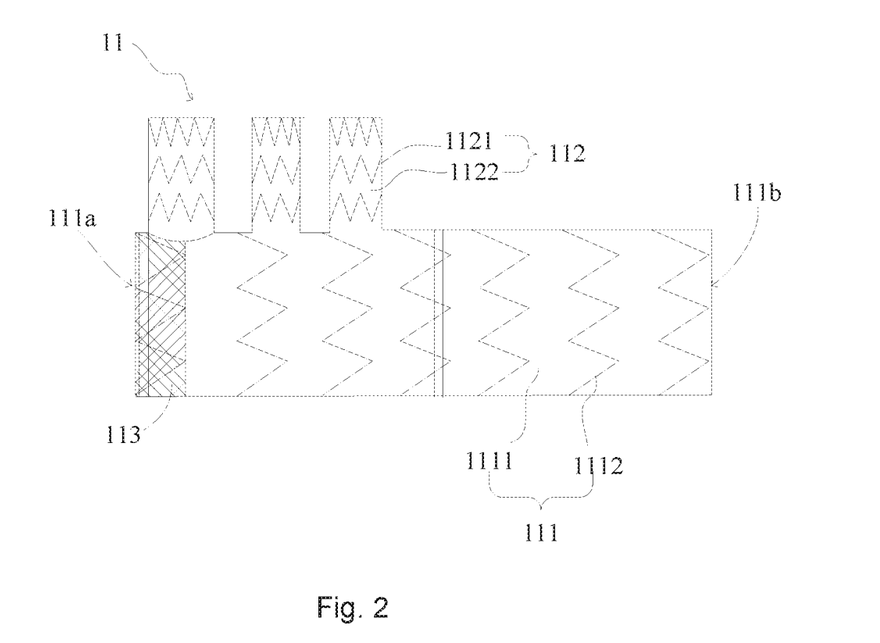
FIG. 2 is a structural diagram of a distal section of the intraoperative stent of FIG. 1.
Figure 3:
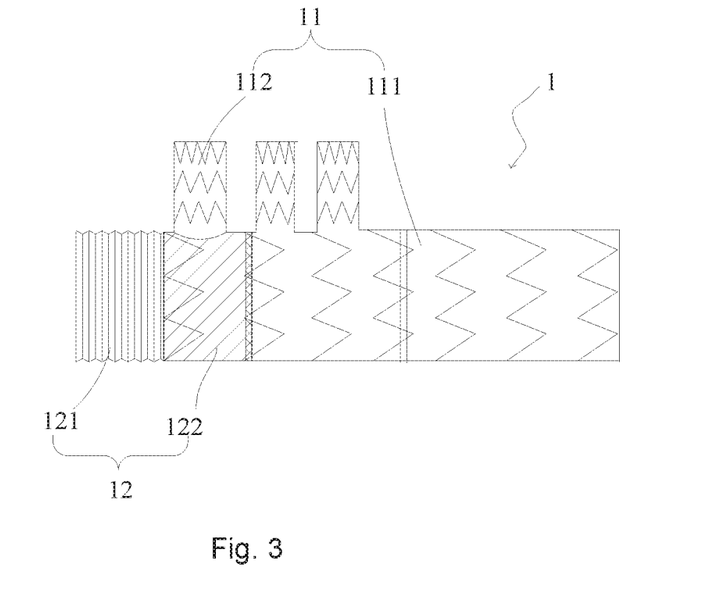
FIG. 3 is a structural diagram of another exemplary intraoperative stent according to the present invention.

FIGS. 1-3 show an exemplary intraoperative stent 1 available for a lesion region of an aortic arch. It should be understood that the intraoperative stent 1 is merely illustrative and is not intended to limit the scope of the present invention, as those skilled in the art may utilize the illustrated intraoperative stent 1 to implement the method according to the embodiments of the present invention to treat diseases (e.g., Stanford A aortic dissection) at an aortic arch or utilize any other suitable stent to implement the method according to the embodiments of the present invention, and these suitable stents will not be enumerated herein. For example, the method according to the embodiments of the present invention may employ the intraoperative stent described in CN201310745529.1 or PCT/CN2014/095609, whose entire disclosures are incorporated herein by reference as though set fully forth herein.

Referring to FIG. 1, the exemplary intraoperative stent 1 (hereinafter "stent 1") successively includes a distal section 11 and a proximal section 12 in an axial direction. The proximal section 12 is axially connected to the distal section 11, and the connection is generally a sealing connection such that the proximal section 12 is in communication with the distal section 11 in the axial direction. The stent 1 forms a new blood passage after implantation in a human body. The new blood passage is peripherally sealed, so that the blood flows from the proximal section 12 to the distal section 11.

Referring to FIG. 1 and FIG. 2, the distal section 11 of the stent 1 is sized and configured to fit a natural human aortic arch and includes a main body 111 and at least one branch 112. According to the involvement condition of the lesion, it is optional to arrange one to three branches 112, any one of which is in communication with the main body 111. The main body 111 may be radially compressed and radially expanded. That is, the main body 111 may be radially compressed into a sheath canal, then delivered to a lesion region in vivo through the sheath canal, and radially expanded through mechanical inflation (e.g., balloon inflation) or self-expanding after being released from the sheath canal, so as to cling to the wall and thus be fixed in the vessel. For example, the main body 111 may be prepared from shape memory alloy material (e.g., nickel-titanium alloy) such that the main body 111 has radial self-expanding performance. Similarly, the branch 112 may be radially compressed and radially expanded. That is, the branch 112 may be radially compressed into a sheath canal, then delivered to a lesion region in vivo through the sheath canal, and radially expanded through mechanical inflation (e.g., balloon inflation) or self-expanding after being released from the sheath canal, so as to cling to the wall and thus be fixed in the vessel. For example, the branch 112 may be prepared from memory alloy material (e.g., nickel-titanium alloy) such that it has radial self-expanding performance.

Specifically, with regard to the distal section 11, the main body 111 includes a plurality of waveform rings 1112 successively arranged in an axial direction, and a cover film 1111 covering the waveform rings 1112. The waveform rings 1112 may be made from nickel-titanium alloy such that the waveform rings 1112 have self-expanding performance and may be self-expanded from a radially compressed state to a radially expanded state. The cover film 1111 may be an ePTFE film or a PET film for covering at least one of the inner surface and outer surface of the main body 111. Any branch 112 includes a plurality of waveform rings 1121 successively arranged in an axial direction, and a cover film 1122 covering the waveform rings. The waveform rings 1121 may be made from nickel-titanium alloy such that the waveform rings 1121 have self-expanding performance and may be self-expanded from a radially compressed state to a radially expanded state. The cover film 1122 may be an ePTFE film or a PET film for covering at least one of the inner surface and outer surface of the branch 112.

The main body 111 includes a proximal orifice 111a and a distal orifice 111b. The proximal orifice 111a is connected to the proximal section 12, while the distal orifice 111b is opened. A proximal fabric 113 is provided at the proximal orifice 111a of the main body 111, and the proximal fabric 113 at least covers an inner wall of a region near the proximal orifice 111a, and, of course, may cover an outer wall in the same region so as to form a sandwich structure together with the main body 111. The proximal fabric 113 is an inelastic polyester fabric, for example, a plain polyester fabric or a thread polyester fabric. The proximal fabric 113 may be sutured with the waveform rings 1112 of the main body 111 and thus fixed on the main body 111. The proximal fabric 113 is not required to be too long in the axial direction, for example, without the need to cover the whole inner wall of the main body 111. A distal edge of the proximal fabric 113 generally does not extend beyond a distal edge of the branch 12 closest to the proximal orifice 111a.

Referring to FIG. 1, the proximal section 12 is a tube body that may be made from an inelastic polyester fabric, for example, a plain polyester fabric or a thread polyester fabric, so that it is advantageous for the suturing of the proximal section 12 with the vessel. During suturing, the plain polyester fabric is unable to maintain a stereoscopic structure and can easily collapse, so that it is inconvenient for a surgeon to perform a suturing operation; however, the thread polyester fabric may always maintain a tubular structure and a thread folded structure when in use, so that it is convenient for a surgeon to insert a needle, quickens the suturing speed and reduces the operation time.

The distal orifice of the proximal section 12 may be connected to the proximal orifice of the main body 111 of the distal section 11, so that the proximal section 12 and the distal section 11 are not overlapped with each other in the axial direction after the both are communicated with each other. Alternatively, the proximal section 12 further has a partially axial region covering a part of the outer surface of the distal section 11. For example, referring to FIG. 3, the proximal section 12 successively includes a first portion 121 and a second portion 122 in the axial direction. The first portion 121 is located on a proximal side with respect to the main body 111 and is suspended, while the second portion 122 covers at least one partially axial region of the main body 111 and is in connection (e.g., suturing connection) to the main body 111 from the outer wall of the main body 111. The second portion 122 is not required to be too long, for example, without the need to cover the whole wall of the main body 111. A distal edge of the second portion 122 generally extends slightly beyond a distal edge of the first branch 122 starting from the proximal end.

The method according to the embodiments of the present invention may be implemented by using the intraoperative stent 1 or any other suitable stent. In the method according to the embodiments of the present invention, a diseased thoracic aorta is first exposed from a thoracic cavity. The exposed thoracic aorta includes at least an ascending aorta and an aortic arch. For example, the thoracic aorta may be exposed by median sternotomy.

Figure 4:
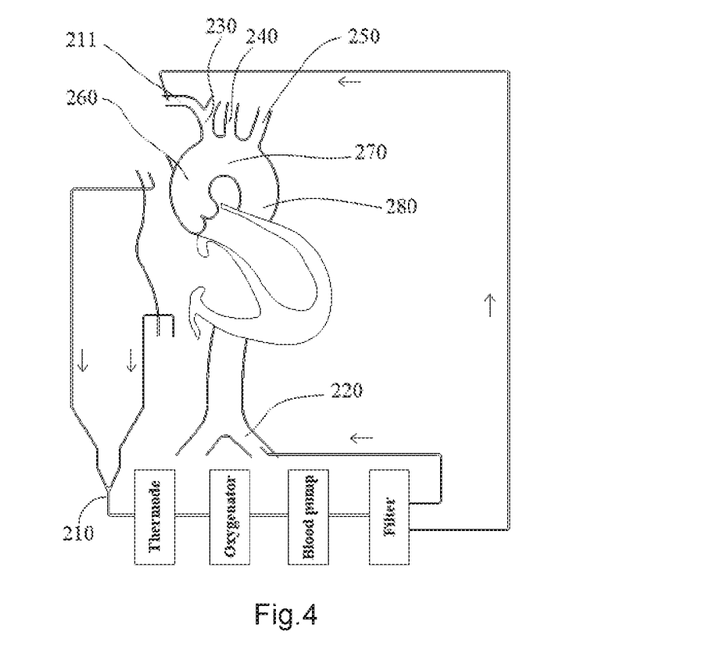
FIG. 4 is a schematic diagram showing the establishment of an extracorporeal circulation in a method according to an embodiment of the present invention.

Second, an extracorporeal circulation is established. The extracorporeal circulation may be established by using an existing conventional method. For example, referring to FIG. 4, a blood flow 210 (as shown by the arrow) from precava and postcava flows into an extracorporeal circulation device. The extracorporeal circulation device may be any suitable existing device, and, for example, may successively include a thermode, an oxygenator, a blood pump and a filter in a blood flow direction. The blood flow output from the extracorporeal circulation device is divided into two paths, one of which is delivered to the left femoral artery or right femoral artery 220 to establish a low body perfusion, while the other one may be delivered through the right axillary artery 211 for cerebral perfusion. Then, a conventional myocardial protection can be performed. For example, myocardial protection liquid may be directly perfused through openings in the left coronary artery and right left coronary artery, or continuously perfused through the right atrium retrograde coronary sinus perfusion.

Figure 5:
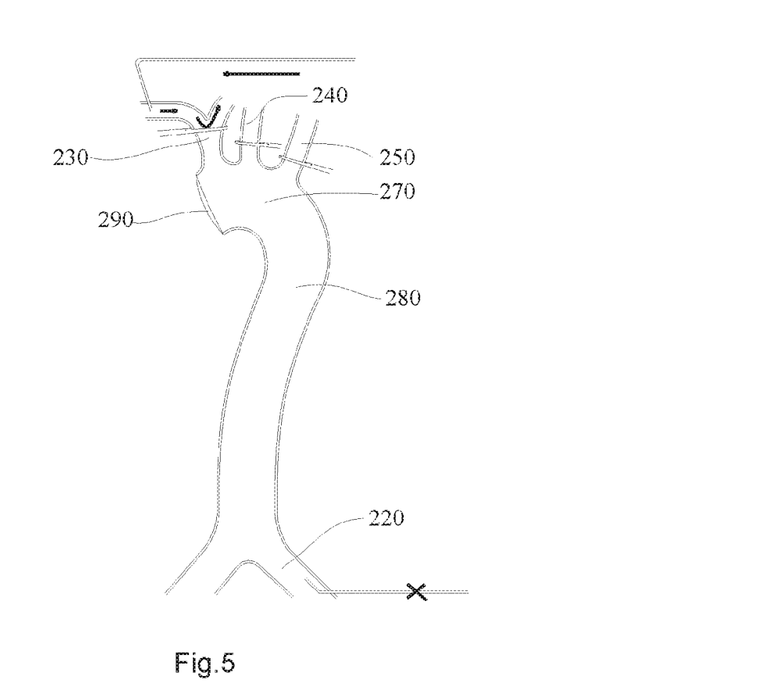
FIG. 5 is a schematic diagram illustrating the forming of an incision on a thoracic aorta of FIG. 1.

In the next step, an incision is formed on an ascending aorta 260. The incision may be a through hole formed on a wall of the ascending aorta 260, or a partial orifice or complete orifice of the ascending aorta 260 formed by cutting the cross-section of at least one part of the ascending aorta 260. Referring to FIG. 5, the low body perfusion is stopped after forming the incision, for example, the perfusion of femoral artery 220 is stopped. Meanwhile, the flow of cerebral perfusion (i.e., the flow of perfusion of right axillary artery 211) is reduced to below a normal flow, for example, to 300-600 ml/min. In the implementation shown in the present invention, the ascending aorta 260 is completely separated by cutting the cross-section of the whole ascending aorta 260 so as to expose the whole cross-cut orifice as the incision 290. For a patient having an aortic arch lesion, a large part of the lesion region will be extended to the ascending aorta 260, so it is possible to perform the replacement of the ascending aorta 260. The entire cutting of the ascending aorta 260 facilitates the replacement or reconstruction of the ascending aorta 260.

The following embodiments or implementations will be described on the basis of the incision 290 shown in FIG. 5. It should be understood that this incision 290 is merely illustrative and not intended to limit the scope of the present invention, as those skilled in the art may select a suitable formation mode of the incision 290 according to the actual conditions of the ascending aorta 260. For example, if the ascending aorta 260 has been involved and diseased, the incision 290 may be formed by a complete cross-sectional cut; if the ascending aorta 260 is still well-maintained and is not obviously diseased, a through hole may be formed on the wall of the ascending aorta 260 to serve as the incision; other conditions will not be enumerated. Furthermore, an opening of any arch branch vessel (a connection port with the aortic arch) is substantially unexposed by the incision.

After the incision 290 is formed, a distal section 11 of an intraoperative stent (e.g., any intraoperative stent 1 shown in FIGS. 1-3) is delivered to the aortic arch of the thoracic aorta (including an aortic arch and at least one arch branch vessel) through the incision 290 by an endovascular technique and then radially expanded. To facilitate the convenience of stent implantation, referring to FIG. 6, it is required to open the arch branch vessel to facilitate the implantation of the branch 112 of the stent 1, and the guarantee of continuous implementation of cerebral perfusion through the right axillary artery. Therefore, it is required to block an unknown artery 230 at a junction of the unknown artery 230 and the right axillary artery, so that sufficient implantation space is reserved for the branch 112 that may be implanted into the unknown artery 230. During this process, the perfusion flow of the cerebral perfusion through the right axillary artery is still maintained to be less than a normal flow, and the low body perfusion through the femoral artery 220 is still in a closed state. The endovascular technique includes: radially compressing the intraoperative stent into a sheath canal and delivering the intraoperative stent in a vessel through the sheath canal, so that the stent may be delivered to an aortic arch lesion location and then released at the lesion location so as to be radially expanded and fixed in the vessel. Specifically, Chinese patent document CN201110133682.X discloses a conveyor suitable for conveying an intraoperative stent, and the techniques illustrated in this reference may be implemented herein.

Figure 7:
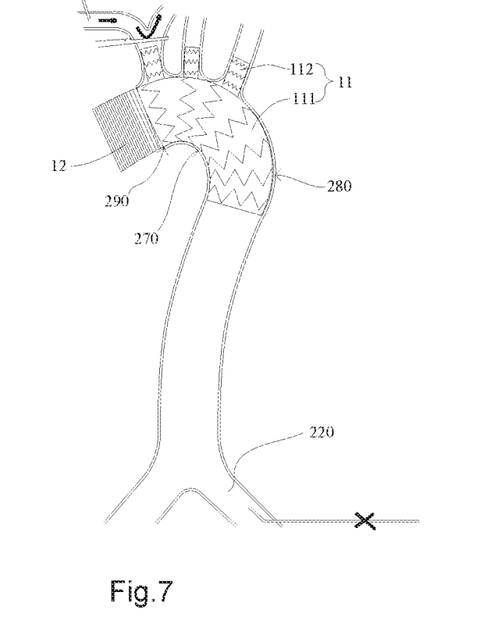
FIG. 7 is a schematic diagram after the intraoperative sent is implanted in the thoracic aorta from the incision.

Referring to FIG. 7, after the intraoperative stent 1 is implanted, at least one part of the proximal section 12 is retained outside the incision 290 and suspended. The main body 111 of the distal section 11 is radially expanded in the thoracic aorta. For example, the main body 111 may be expanded at the aortic arch 270 only. If the lesion extends to a descending aorta 280 from the aortic arch 270, the main body 111 may be expanded in both the aortic arch 270 and the descending aorta 280. At least one branch 112 of the distal section 11 is radially expanded in a corresponding arch branch vessel. One to three branches may be selected according to the actual lesion shape of the arch, and then are expanded in corresponding arch branch vessels, respectively. In FIG. 7, three arch branch vessels are all implanted with the branches 112 of the intraoperative stent.

After the distal section of the intraoperative stent is released and expanded, the thoracic aorta is blocked between the incision and the arch branch vessel closest to the incision. In this embodiment, the thoracic aorta is blocked between the unknown aorta 230 and the incision 290. Specifically, the thoracic aorta at the blocked position is implanted with the intraoperative stent. When the thoracic aorta is blocked from the outer wall of the thoracic aorta, the intraoperative stent at this position is also blocked. For example, a proximal opening of the intraoperative stent may be blocked, so that the blood is prevented from flowing from this blocked position. For example, at the blocked position, the thoracic aorta and the intraoperative stent in the thoracic aorta may be blocked by tying the thoracic aorta with a band, or by gripping the thoracic aorta with a pair of forceps. It should be understood that, depending on the different locations of the incision, the blocked position may be in the ascending aorta or in the aortic arch.

Figure 8:
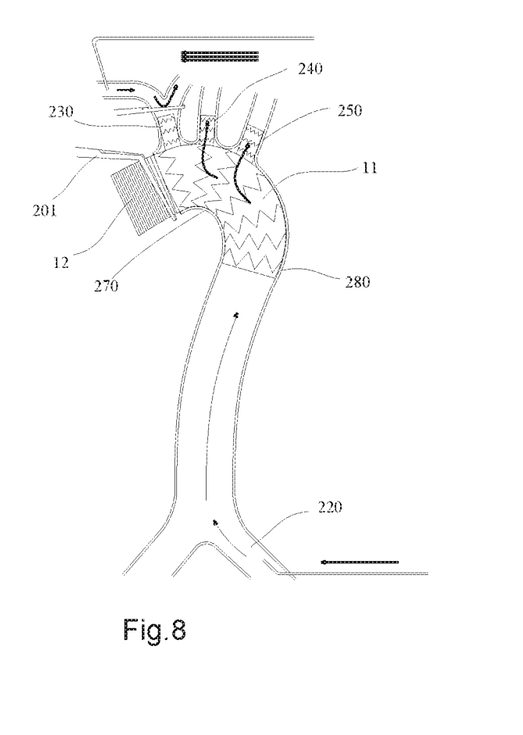
FIG. 8 is a schematic diagram showing the blocking of the implanted thoracic aorta of FIG. 7.

FIG. 8 shows that the thoracic aorta is gripped with a pair of forceps 201. The intraoperative stent implanted in the thoracic aorta may be the exemplary intraoperative stent 1 shown in FIG. 2. For example, the intraoperative stent 1 may be gripped near the proximal orifice 111a of the distal section 11 of the intraoperative stent 1 while the thoracic aorta is gripped at the blocked position. Specifically, an inelastic polyester fabric is provided on an inner wall of the intraoperative stent 1 near the gripped proximal orifice 111a. During gripping, as the friction between the inner wall and the polyester fabric is large and the wall thickness of the stent at this location is increased, the blocking and sealing performance may be improved, and the blockage failure is avoided as far as possible due to slipping. In addition, the polyester fabric may protect the cover film 1111 of the stent 1 during blockage, so that the isolation failure of the cover film 1111 after implantation due to perforation or tearing resulted from mutual friction is avoided. In addition, the structure shown in FIG. 3 may be imported on this basis. That is, a part of the inelastic polyester fabric of the proximal section 12 covers a region near the proximal orifice 111a of the distal section 11, and the inner wall and outer wall of a gripped position are covered with the polyester fabric. As the outer wall is provided with the polyester fabric, a pair of forceps may apply a uniform force to the polyester fabric on the outer wall, so that a local force is avoided from being applied to the waveform rings and a better sealing effect may be thus formed by uniformly applying a force. It should be understood that the process of tying blockage by a band is similar to the process of gripping blockage by a pair of forceps and may generate equivalent effects, so the tying with a band will not be separately described herein.

After blockage, the thoracic aorta and the proximal opening of the intraoperative stent are closed, and the low body perfusion is recovered at this moment. For example, the femoral artery perfusion at the femoral artery 220 is recovered. Meanwhile, the flow of the cerebral perfusion through right axillary artery is recovered to the normal flow, an exhaust operation is activated (that is, air is exhausted from the un-blocked arch branch vessel), and the human body temperature is recovered. For example, by comparing FIG. 7 with FIG. 8, "x" on one path of blood flowing in the femoral artery 220 in FIG. 7 indicates that the perfusion is in a closed state; while in FIG. 8, an arrow on one path of blood flowing in the femoral artery 220 indicates that the perfusion is recovered to an opened state. The same marks are used in other figures, and will not be repeated here.

Figure 9:
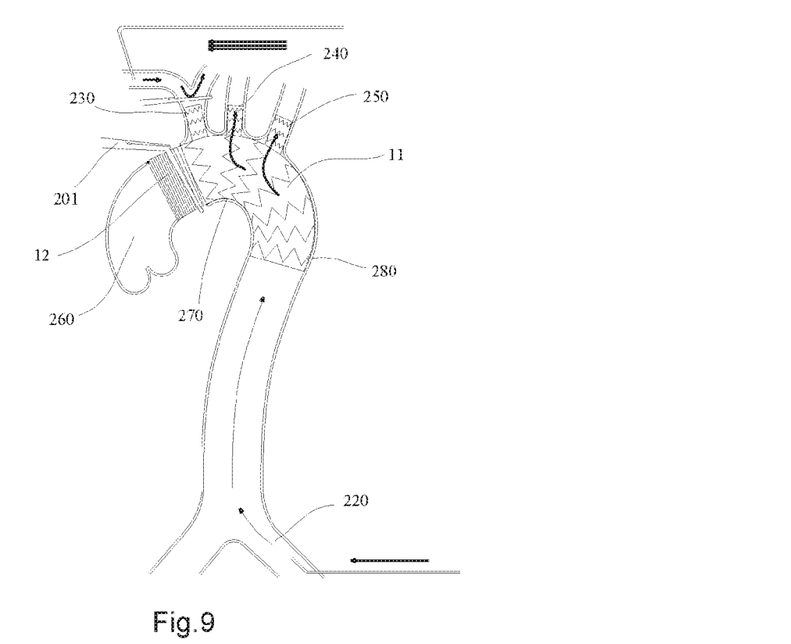
FIG. 9 is a schematic diagram showing the anastomosing of an ascending aorta with the intraoperative stent.

Referring to FIG. 9, after the low body perfusion is recovered, the freely suspended proximal section 12 of the intraoperative stent (located on the proximal side of the blocked position) is imported in the ascending aorta 260 on the proximal end of the incision 290. In this specific implementation, this part of the ascending aorta 260 is an ascending aorta 260 completely separated during the formation of the incision 290 or an artificial vessel in place of the separated ascending aorta 260, which are all collectively referred to as the ascending aorta 260. After the outer wall of the proximal section 12 of the intraoperative stent is adaptively fitted with the inner wall of the ascending aorta 260, the imported proximal section 12 is surgically anastomosed with the ascending aorta 260, and the incision 290 is closed. The surgical anastomosis comprises at least one of suturing, binding, winding with a thread, gripping and splicing. At the end of anastomosis, then blockage of the thoracic aorta may be released; meanwhile, the blockage of the intraoperative stent at this position is released, the blockage of the unknown artery 230 is released, and the normal circulation around the body and the body temperature are recovered. Finally, thorough hemostasia and closing of the thoracic cavity are performed by conventional aortic arch 270 replacement.

Figure 6:
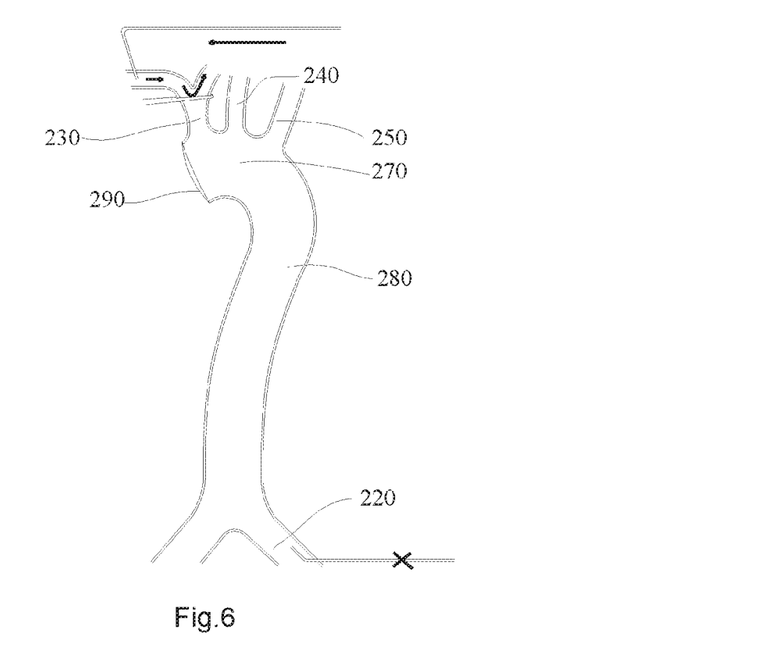
FIG. 6 is a schematic diagram illustrating the releasing of the left common carotid artery and the left subclavian artery after forming the incision in FIG. 5.
Figure 10:
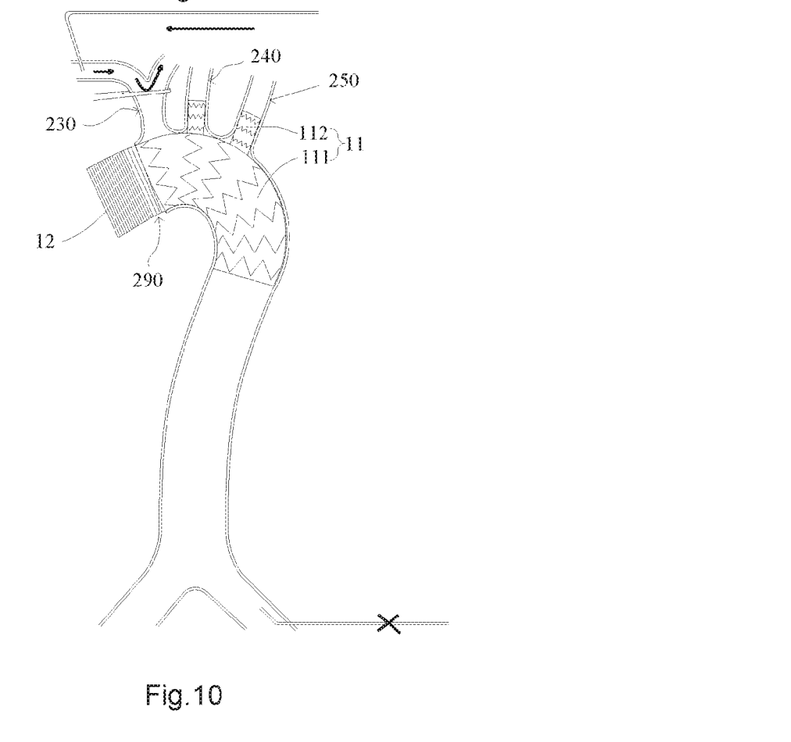
FIG. 10 is a schematic diagram showing the implanting of two arch branch vessels in a branch.

FIGS. 6-8 show that three arch branch vessels are implanted with branches 112, but some patients are only required to be implanted with one or two branches rather than three branches 112. For example, referring to FIG. 6 and FIG. 10, in the case where branches 112 are only implanted in left common carotid artery 240 and left subclavian artery 250, referring to FIG. 6, the unknown artery 230 is still blocked before implantation, and the left common carotid artery 240 and left subclavian artery 250 to be implanted with the branches 112 remains unblocked. A difference between this case and the case where three arch vessels are required to be implanted with branches lies in that, referring to FIG. 11, the branches 112 are subsequently implanted in the left common carotid artery 240 and left subclavian artery 250 only. During a subsequent operation, the unknown artery 230 continues to be blocked. After the ascending aorta 260 is completely anastomosed with the intraoperative stent and the incision 290 is closed, the unknown artery 230 without any branch implanted therein is cut at its cross-section, the unknown artery 230 is anastomosed with the ascending aorta 260, and the opening of the original unknown artery 230 is occluded by the cover film of the intraoperative stent.

Figure 11:
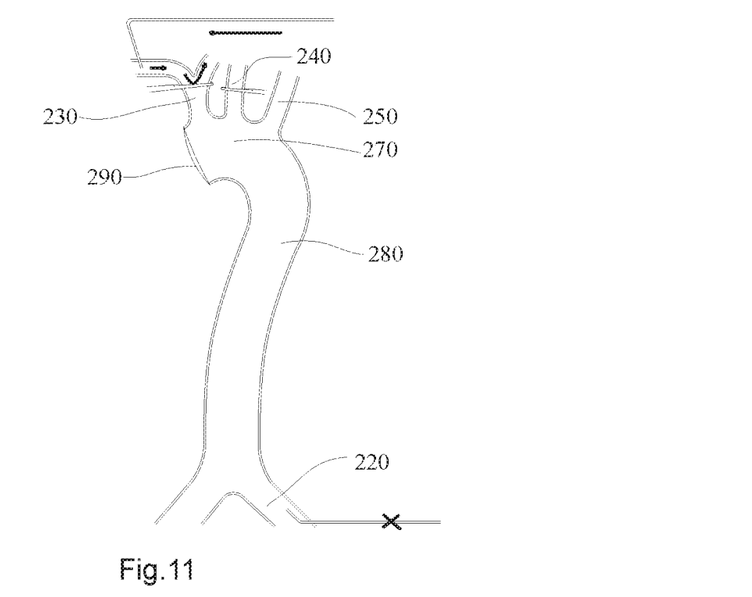
FIG. 11 is a schematic diagram showing the implanting of one arch branch vessel in a branch.
Figure 12:
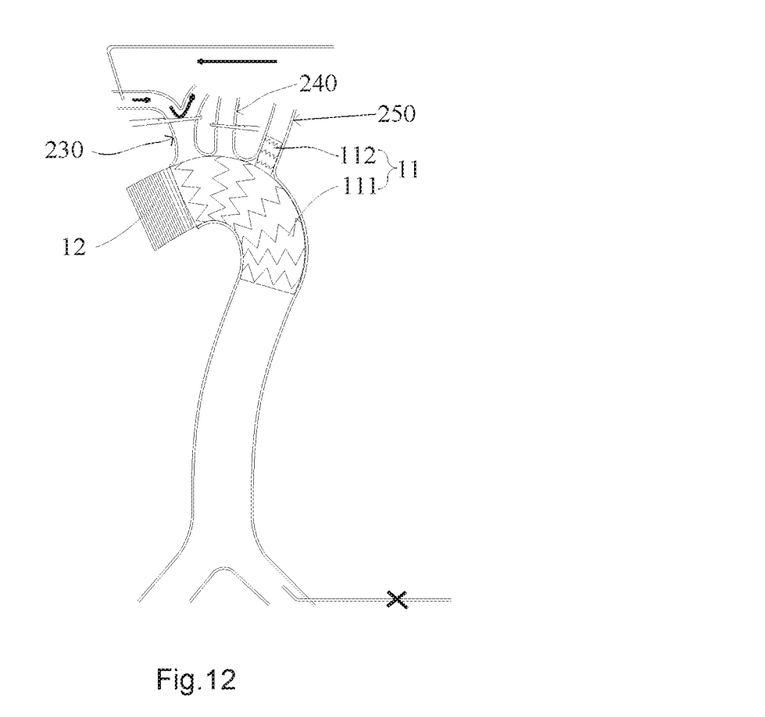
FIG. 12 is a schematic diagram after one arch branch vessel is implanted in the branch of FIG. 11.

For another example, referring to FIG. 11 and FIG. 12, in the case where only one branch 112 is required to be implanted in left subclavian artery 250, referring to FIG. 11, the difference is that the unknown artery 230 and the left common carotid artery 240 are blocked before implantation, and the left subclavian artery 250 to be implanted with the branch 112 remains unblocked. Referring to FIG. 13, subsequently, the branch 112 is implanted in the left subclavian artery 250. During a subsequent operation, the unknown artery 230 and the left common carotid artery 240 continue to be blocked. After the ascending aorta 260 is completely anastomosed with the intraoperative stent and the incision 290 is closed, the unknown artery 230 and the left common carotid artery 240 both without any branch implanted therein are cut at their cross-sections respectively, the unknown artery 230 and the left common carotid artery 240 are respectively anastomosed with the ascending aorta 260, and the opening of the original unknown artery 230 and the opening of the left common carotid artery 240 are occluded by the cover film of the intraoperative stent.

In the method provided by the present invention, after an intraoperative stent is released and expanded in an aorta and at least one arch branch vessel and before the vessel is exactly anastomosed with an incision, by blocking a thoracic aorta between the incision and an arch branch vessel closest to the incision, the intraoperative stent in the thoracic aorta is also blocked, so that blood is prevented from flowing from the incision and a proximal orifice of the intraoperative stent, and the low body perfusion, for example, femoral artery perfusion, may be recovered in advance, thereby reducing the circulatory arrest time of the low body perfusion and reducing the time of ischemia of visceral organs and lower limbs of a patient. Meanwhile, the cerebral perfusion flow through the right axillary artery may be recovered to a normal flow in advance, and the time of ischemia of the brain of the patient is reduced.

The invention claimed is:

1. A method for treating an aortic arch disease, characterized in that it comprises the following steps of:
   establishing an extracorporeal circulation, the extracorporeal circulation comprising a low body perfusion and a normal-flow cerebral perfusion;
   forming an incision on an ascending aorta, and stopping the low body perfusion at the same time;
   delivering a distal section of an intraoperative stent into an aortic arch and at least one arch branch vessel through the incision by an endovascular technique, and radially expanding the distal section of the intraoperative stent;
   blocking a thoracic aorta between the incision and the arch branch vessel closest to the incision;
   recovering the low body perfusion;
   surgically anastomosing a proximal section of the intraoperative stent with the ascending aorta and closing the incision; and
   releasing the blocked thoracic aorta.

2. The method for treating an aortic arch disease according to claim 1, wherein the forming of an incision on an ascending aorta comprises: cutting the ascending aorta along a cross-section of the ascending aorta, or forming a through hole on a wall of the ascending aorta.

3. The method for treating an aortic arch disease according to claim 1, wherein the endovascular technique comprises: radially compressing the intraoperative stent into a sheath canal and delivering the intraoperative stent into a vessel through the sheath canal.

4. The method for treating an aortic arch disease according to claim 1, wherein the flow of the cerebral perfusion is reduced while forming the incision.

5. The method for treating an aortic arch disease according to claim 1, wherein an opening of any arch branch vessel is unexposed by the incision.

6. The method for treating an aortic arch disease according to claim 1, further comprising the following step of: exhausting air after blocking a thoracic aorta between the incision and the arch branch vessel closest to the incision.

7. The method for treating an aortic arch disease according to claim 1, wherein the method further comprises: tying by a band or gripping by a pair of forceps the thoracic aorta between the incision and an arch branch vessel closest to the incision to block the thoracic aorta and the intraoperative stent in the thoracic aorta.

8. The method for treating an aortic arch disease according to claim 4, further comprising the following step of: recovering the flow of the cerebral perfusion to a normal flow after blocking a thoracic aorta between the incision and the arch branch vessel closest to the incision.

9. The method for treating an aortic arch disease according to claim 1, wherein the surgical anastomosis comprises at least one technique selected from the group consisting of suturing, binding, winding with a thread, gripping and adhesive bonding.

* * * * *